United States Patent [19]

Villasenor et al.

[11] 4,406,285
[45] Sep. 27, 1983

[54] MANUAL RADIAL AND CHORDAL KERATOTOMY APPARATUS

[75] Inventors: Richard A. Villasenor, 14935 Rinaldi St., Mission Hills, Calif. 91345; Leonard L. Krasnow, Worchester, Mass.

[73] Assignee: Richard A. Villaseñor, Mission Hills, Calif.

[21] Appl. No.: 227,709

[22] Filed: Jan. 23, 1981

[51] Int. Cl.³ .............................................. A61F 17/32
[52] U.S. Cl. ................................ 128/305; 128/303 R; 33/21 R; 33/1 B; 33/174 B
[58] Field of Search .................... 128/1 R, 305, 303 R, 128/305.1; 99/537; 83/565; 409/130; 33/1 F, 1 SA, 21 R, 21 B, 174 D, 174 A, 174 B, 174 E, 174 G, 1 B; 604/116, 117; 433/72, 176

[56] References Cited

U.S. PATENT DOCUMENTS

| | | | |
|---|---|---|---|
| 3,074,407 | 1/1963 | Moon et al. | 128/303 R |
| 3,945,117 | 3/1976 | Beaver | 128/305 |
| 4,192,312 | 3/1980 | Wilson | 128/303 R |
| 4,205,682 | 6/1980 | Crock et al. | 128/305 |
| 4,340,059 | 7/1982 | Mavinoff | 128/305 |

FOREIGN PATENT DOCUMENTS

| | | | |
|---|---|---|---|
| 2300326 | 9/1976 | France | 33/1 F |
| 725747 | 4/1980 | U.S.S.R. | 33/174 B |

OTHER PUBLICATIONS

Schachar et al., Radial Keratotomy, "Proceedings of the Semi-Annual Keratorefractive Society Meeting on the Controversial Aspects of Radial Keratotomy," LAL Publishing, P.O. Box 1225, Denison, Texas 75020, 1980, pp. 201–212.
"Shaping up the Blurry Eye" Toufeas et al., Time Magazine, New York, Sep. 22, 1980.

Primary Examiner—Richard J. Apley
Assistant Examiner—J. L. Kruter
Attorney, Agent, or Firm—Wm. Jacquet Gribble

[57] ABSTRACT

A cornea is altered in shape by providing a template body to guide a surgical blade, the body being formed in a semi-spherical hollow with the outer wall concentric with the inner surface of the cornea and the inner wall of the template body concentric with the outer surface of the cornea. The template body affords a rest surface for a shoulder on the surgical blade to limit penetration of the blade into the cornea in accordance with the thickness of the template body, which varies inversely with the thickness of the cornea to preclude blade penetration of the anterior chamber of the eye behind the cornea. Guide slits in various patterns are formed in the template body between the optic zone and the limbus circles diameter of the eye to change the resistance of the cornea to inner eye pressures and thus alter the corneal shape to correct focal problems of the eye.

6 Claims, 10 Drawing Figures

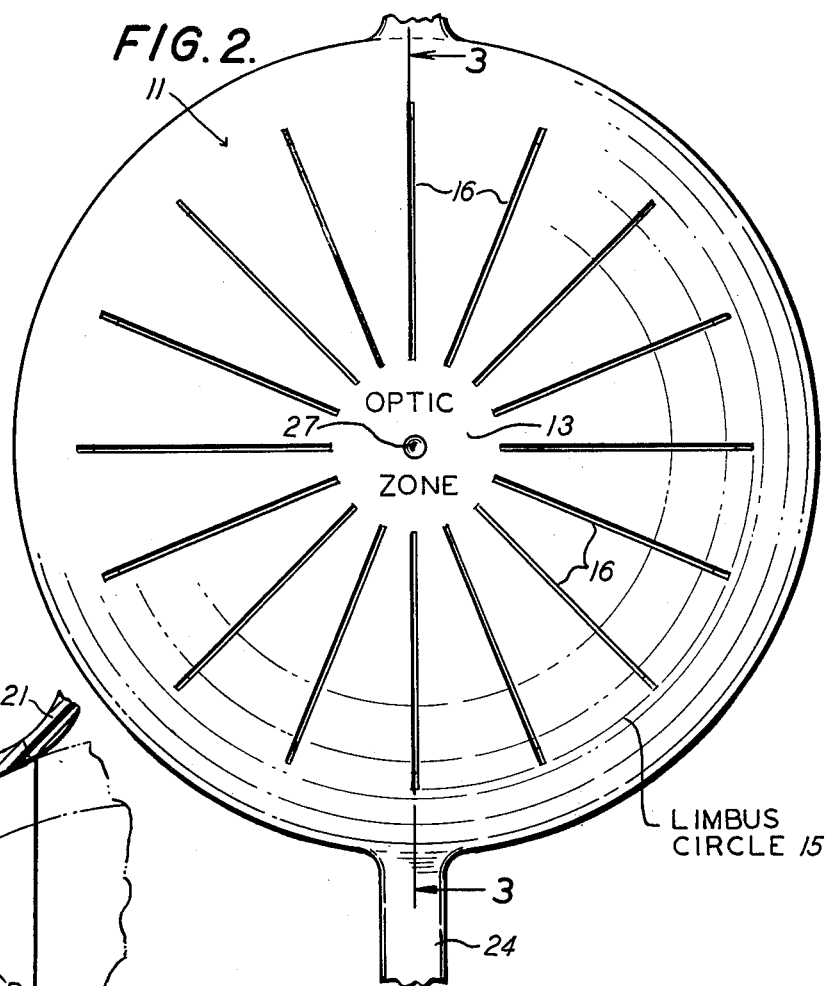

METHOD L
1.25 - 2.00 D
MEAN Δ DIOPTER = 1.68 D

METHOD B
2.25 - 2.50 D
MEAN Δ DIOPTER = 1.80 D

METHOD TL
2.75 - 3.5 D
MEAN Δ DIOPTER = 3.0 D

METHOD TR
3.75+ D
MEAN Δ DIOPTER = 3.69 D

MANUAL RADIAL AND CHORDAL KERATOTOMETRY APPARATUS

BACKGROUND OF THE INVENTION

While many attempts over the past years have been made to correct surgically the vision defects detected by refractive examination instead of corrective glasses or contact lenses, it is only since the work of Dr. Sato of Japan was refined by Dr. Fydenoy of Russia that numbers of researchers and doctors in the field have resorted to surgical techniques with some degree of permanent success one promising procedure is defined as "manual radial keratotometry" wherein a plurality of deep radial cuts are made in the cornea of an eye which refraction has shown to be myopic to allow internal eyepressure to alter the corneal curvature to correct the visual defect the cornea heals quickly compared to other types of tissue, and the scar tissue from the surgery does not interfere with later sight and is not obvious to an observer farther from the eye than two feet while there is some danger of infection, as from any surgical procedure, and differing periods for healing, freedom from the need to wear corrective glasses or contact lenses is of greater value to persons in certain professions, and has important psychological advantages for other persons.

One problem with manual keratotometry in the past has been the control of the depth of the incision, since too deep a cut may damage the endothelium layer of the corneal inner surface and the blade penetrates the Descemet membrane into the anterior chamber of the eye. The endothelium is essential to the general health of the eye and cell loss is permanent. On the other hand, if the incision is shallow, the correction may not be permanent. Since the thickness of the cornea increases from the central optic zone to the circle of the limbus, the edge of the cornea, it is not possible to merely carefully set the extension of the cutting point from the guard or shoulder of the special scalpel to limit penetration. While pachometry procedures can accurately guage the thickness and profile curvature of the cornea there are few practitioners capable of translating such parameters into manual controls to effect radial or chordal incisions of sufficient exactness as to accomplish the precise correction dictated by the refractive, pachometric and keratometric measurements.

Therefore the method and apparatus of the invention are purposed to overcome the possible imprecision of purely manual keratotometry and to provide a method and apparatus aiding the surgeon to operate simply and with precision, minimizing danger to the eye and to the success of the procedure. The operation is one capable of being performed in properly equipped doctor's offices and outpatient clinics under topical anesthetic with anesthesia standby.

BRIEF DESCRIPTION OF THE INVENTION

The invention relates to manual keratotometry and more particularly to manual keratotometry employing a mass-producible template for guiding the surgical blade and the method for using the apparatus.

The depth of the incision and the location on the cornea of the incisions are critical. Therefore, the apparatus of the invention comprises a preferably molded template body with semi-spherical walls defining a shell of varying thickness from a central optic zone to a periphery beyond the diameter of the limbus circle of the eye. The central zone is marked with a visible indicator to aid in placement of the template on the eye. Fixation means such as finger grips or suction cups are at the periphery of the template body. The curvature of the obverse or outer surface of the body is concentric with the inner or endothelium contour of the cornea, while the reverse or inner surface of the template body is concentric with the outer contour of the cornea. Pairs of parallel walls in the template body define guide slits for the surgical blade in the zone between the optic zone circle and the limbus circle diameters. The guide slits extend through the template body and may be radial, chordal or both, in accordance with the vision defect to be corrected. The template body may be molded of plastic or stamped from metal, both of which materials are capable of sterilization without harm to the device.

The process of the invention for keratotometric correction of corneal curvature using a shouldered or guarded blade with adjustable blade extension beyond the shoulder and employing a blade template shaped in accordance with refractive and pachometric data for the subject eye includes the steps of forming obverse and reverse surfaces on a template body which are, respectively, concentric with the inner and outer contours of the cornea. A plurality of parallel pairs of walls are formed in the template body to define guidance slits the depth of the body in accordance with the corrective pattern for flattening the corneal curve determined by the refractive and pachometric data derived from the subject eye, and incisions are made in the cornea guided as to pattern and depth by the template body contact with the shouldered or guarded blade. The incisions are treated antiseptically and the template removed from the eye.

The inventive apparatus and process afford simple precise means for making more accurate a simple procedure without undue complication. The data necessary for forming the templates is the same data needed for the procedure. Templates may be made up from average parameters in a range of dimensions and blade extensions adjusted to compensate for subject cornea deviation from the average. The apparatus may be molded economically from methyl acrylate or other like plastic polymers. Alternatively the template may be of metal which could be re-sterilized by autoclaving. In either material cost would be nominal and accuracy assured.

These and other advantages of the invention are apparent from the following detailed description and drawing.

BRIEF DESCRIPTION OF THE DRAWING

FIG. 1 is a plan view of a template for radial keratotometry in accordance with the invention;

FIG. 2 is a fragmentary plan view of the embodiment of FIG. 1 to a greater scale;

FIG. 3 is a fragmentary sectional elevational view taken along line 3—3 of FIG. 2 showing the association between the device of the invention and a subject cornea;

FIG. 4 is a schematic sectional view in operational orientation of a subject eye and the embodiment of FIG. 1, both shown fragmentarily;

In the various Figures like reference characters are used to designate like parts.

DESCRIPTION OF THE PREFERRED EMBODIMENTS

Figure 5:
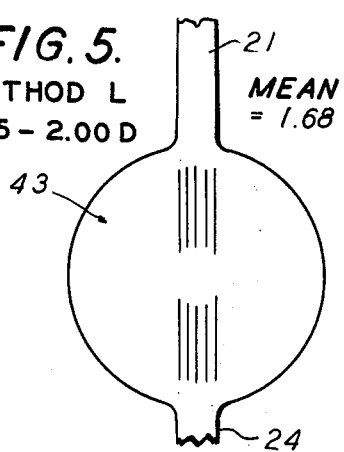
FIGS. 5 through 8 are schematic plan views of templates in accordance with the invention patterned for correction of different vision defects.

The embodiment of FIGS. 1-3 comprises a template 11 having a template body 12 with a central optic zone 13 and a peripheral zone 14. The peripheral zone extends outwardly beyond a limbus circle 15 which defines the outer ends of a plurality of radial guide slits 16 extending from the optic zone. At opposed sides of the template fixation means extend from the template body periphery to define finger and thumb grips 18, 19, respectively. The finger grip has a narrow neck 21 attached to the template body and connecting a finger tab 22 to the body. Thumb grip 19 has a narrow neck 24 attached to the body and connecting an arcuate thumb tab 25 to the body. A central locator index dot 27 in the optic zone, which is a visual index, enables a user to center the template body on the cornea in accordance with the observed optic zone of the eye by means of the fixation tabs 22, 25.

As is best seen in FIG. 3, the template is a semispherical shell with an obverse or outer wall 31 and an inner or reverse wall 32. The walls differ in curvature and the wall thickness of the template body therefore varies from the optic zone to the peripheral template edge 34 outside the limbus circle 15, diminishing in thickness from the optic zone to the periphery. The cornea, on the other hand, increases in thickness from the optic zone to the limbus circle, as is indicated in FIG. 3. In that Figure the curvature of the cornea outer contour is indicated by the arc 32 of the template reverse surface. The inner contour of the cornea is indicated by a broken arc 36, having a radius centered on the visual axis 35 at a point 37. Displaced along the visual axis from point 37 is a point 38, from which a radius B describes the reverse curvature of the template body and the outer contour of the cornea. Curve line 32 coincides with the epithelium layer of the eye while curve line 36 coincides with the endothelium layer within the cornea, which lies between Descemet's membrane and the liquid of the anterior chamber of the eye. The relationships of these members of the eye are schematically shown in the partial sectional view of FIG. 4, wherein the incision in the cornea is shown being made with a surgical blade 39. Thicknesses are exaggerated in FIG. 4 for the sake of graphic exposition.

The radii A, B and C are tabulated below for an average cornea:

A = 7.6 mm
B = 7.5 mm
C = 6.29 mm

The displacement of the radial point 38 on the visual axis from point 37 is 0.66 mm.

One of the important dimensions is the corneal wall thickness, indicated on the axis by dimension V in FIG. 3, which may be 0.55 mm. At ten degree arcuate intervals from the visual axis are dimensions W, X and Y. At 50° from the axis is dimension Z. At each of these dimension points along the corneal vertical arc the pachometric data must be noted, since the increase in corneal thickness from optic zone to periphery may not always be uniform.

As is obvious from FIG. 3, the template thickness at its optic zone may be about 0.67 mm, but may vary from that dimension with the type of blade employed. The other dimensions vary from subject to subject within a definable range.

Again referring to the schematic sectional elevational view of FIG. 4, a template 11 in accordance with the invention is shown in operative position upon a subject eye 41. Central locator index dot 27 in optic zone 13 is centered over the observed optic zone of the eye by means of fixation tabs 22, 25(not shown). The position of locator index dot 27 is normally central of the pupil unless the pupil and the limbus circle are not concentric, in which case allowance must be made, based upon the pachometry data, for the central point of the corneal minimum thickness area. Normally the dot is aligned with the optical axis of the subject eye.

As can be seen from FIG. 4 surgical knife 39 is inserted in a guide slit 16 of template 11, preferably adjacent the optic zone, and plunged into the cornea until the knife point nears the Descemet's membrane. A shoulder 42 of the knife, from which blade 39A projects, rests upon the outer surface 31 of the template and the blade is preferably oriented perpendicular to a tangent to the template curve at the point of knife entry. The blade is then drawn across the surface of the template, guided by the slit walls, or the eye is rotated with respect to the blade, to the termination of the slit adjacent the limbus of the eye. This procedure is accomplished while the template is held in place on the eye by the finger and thumb tabs of the template. Incisions are made successively in line with each template slit, preferably with opposite slits of a diametral pair being utilized in turn, until all of the required incisions are made in the cornea. The template is then removed and the cornea cleansed and antiseptically treated. The depth of each incision is then checked and, if necessary, one or more of the incisions may be deepened.

If the incisions are properly made initially no re-incision is necessary. It has been found that re-cutting to achieve greater incision depth increases the danger of perforation of the eyeball and such perforation can be avoided by initial proper selection of the template and proper setting of knife blade protrusion from the knife shoulder or guide, all with due regard to the pachometric and other data from pre-operative examination.

Figure 6:
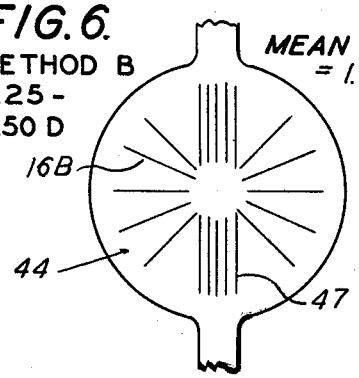
Figure 7:
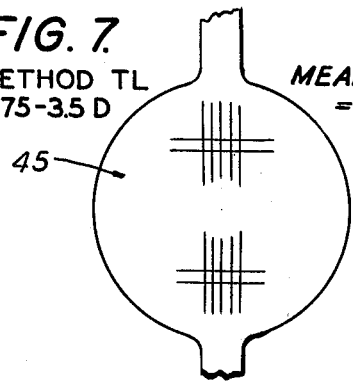
Figure 8:
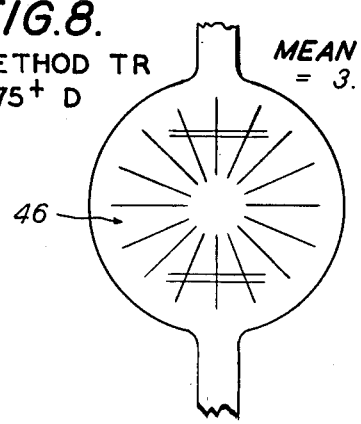

The pattern of guide slits shown in FIGS. 1 and 2 is known in the field of this art as "Method A" and is prescribed for correction of myopia up to 1.00 diopter, with a mean Δdiopter of 0.58. Obviously not every visual correction can be made with the single incision pattern made by template 11 of FIG. 1. Typical alternate patterns are shown in FIGS. 5 through 9, and FIG. 5 shows a guide slit pattern of a template 43 to correct an astigmatic eye. FIGS. 6, 7 and 8 show templates 44, 45 and 46 with alternate incision guide patterns for incising corneas of eyes suffering from both astigmatism and myopia. The prescribed incision pattern and the consequent guide slit pattern of the template varies with the degree of myopia and the axis of astigmatism and each FIG. 5 through 8 has legends setting forth the diopter data from which the pattern derives and the nominal designation of the incision pattern. Thus, FIG. 6 shows a template 44 with guide slit pattern of radial lines 16B and chordal lines 47 designated as Method B, in which the axis of astigmatism is along the axis of the chordal lines. The eye to be corrected has been shown to have a reading of from 2.25 to 2.50 diopters, the mean $\Delta D = 1.80$.

Similar parameters are noted for FIGS. 7 and 8 for templates 45 and 46.

Figure 9:
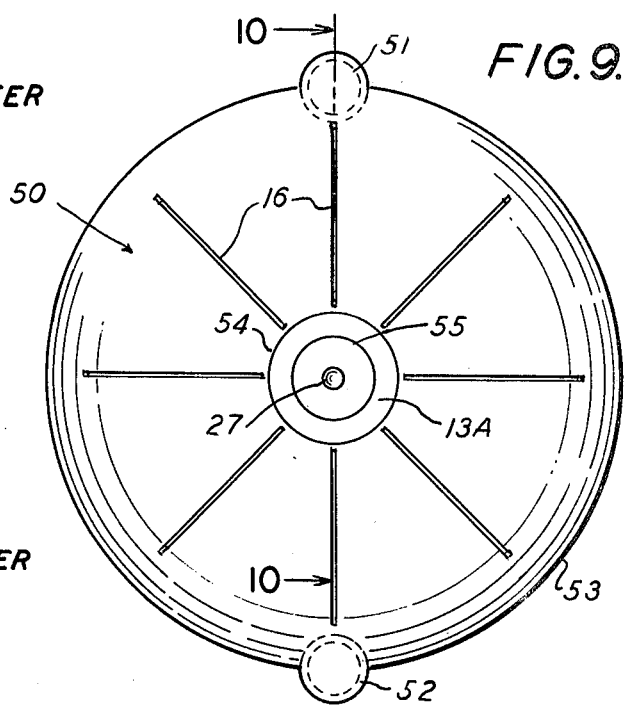
FIG. 9 is a plan view to an enlarged scale of an alternate embodiment of the invention having suction fixation appendages.

FIG. 9 shows an alternate embodiment of the invention wherein a template 50 has a lesser number of radial guide slits than the template of FIG. 1, but still distributed evenly around the surface of the template. Measuring rings such as indicia rings 54, 55 in an optic zone 13A of the template are concentric with indicator dot 27. The rings indicate to the operating surgeon the relationship of the inner optic zone of the subject eye to the terminations of the guide slits, terminating inwardly of the template. The eye optic zone is known from the pachometric data and the rings are of known diameters and standard for all of the templates upon which they appear.

Figure 10:
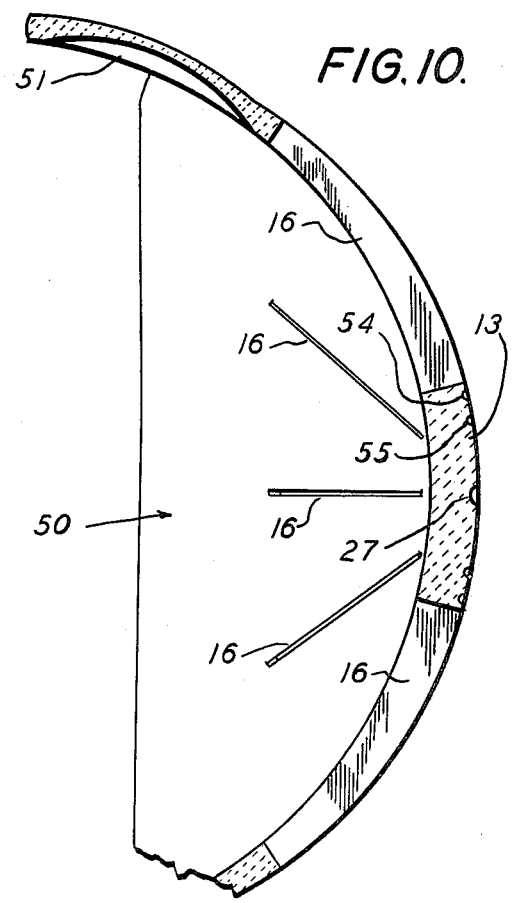
FIG. 10 is a fragmentary sectional elevational view taken along line 10—10 of FIG. 9.

Template 50 has alternate fixation means. Small integral suction cups 51, 52 at diametrically opposed zones on template periphery 53 afford means for fixing the template to the epithelium of the subject eye. Cup 51 is shown to an enlarged scale in the sectional elevational view of FIG. 10, wherein the cup is seen to be shallow and the optic zone 13A is seen to be indented to receive pigment to define indicator dot 27 and the concentric measuring rings 54, 55 which indicate average corneal optic zones.

Both the apparatus and the process of the invention lend themselves to to simple eye surgery with major corrective benefits. While some of the template guide slit patterns for corrective surgery for specific abberations of vision have been discussed, the apparatus and the method disclosed lend themselves to a multiplicity of corrective surgeries that are not defined in this disclosure. The apparatus is inexpensive to fabricate by techniques and of materials presently known, and both the apparatus and the method may be gainfully used by competent surgeons to correct visual defects within the premises of a well equipped clinic or surgeon's office with a preciseness, safety and quickness not heretofore possible.

While the several embodiments illustrated herein encompass many of the correctable visual defects, the disclosure does not exhaust the measure of corrections possible when employing the invention. It is therefore desired that the invention be measured by the appended claims rather than by the foregoing illustrative specification and drawing.

We claim:

1. Apparatus for guiding a surgical knife blade in keratotometry refractive eye surgery comprising a template adapted to fit an eye, a semi-spherical template body, fixation means on the template to secure the template with respect to the eye, a central optic zone on the template body, a visible locator index in the optic zone visible from outside the template, said body having an obverse surface concentric with the inner surface of the cornea and a reverse surface concentric with the outer surface of the cornea, and knife blade guide slits through the body.

2. Apparatus for guiding the path and controlling the penetration of a surgical blade into the cornea of an eye during keratotometry refractive eye surgery for the correction of myopia and astigmatism and comprising a template, a template body, fixation means at the periphery of the template, a central optic zone on the template body, a visible locator index central of the optic zone, parallel walls outside the optic zone defining guide slits in the template area adjacent the optic zone and limited by the limbus circle of the eye cornea being incised, said template body being semi-spherical in shape with obverse and reverse curving surfaces, the obverse surface being concentric with the endothelium contour of the subject eye, and the reverse surface of the template body being concentric with the epithelium contour of the subject eye to control the penetration of the surgical blade, and knife blade guide slits through the template body.

3. Apparatus in accordance with claim 2 wherein the guide slits are defined by spaced, parallel walls extending radially from the optic zone.

4. Apparatus in accordance with claim 2 wherein the guide slits are defined by spaced, parallel wall pairs extending chordally in the template area between the optic zone and the body periphery.

5. Apparatus in accordance with claim 2 wherein the guide slits are defined by spaced pairs of parallel walls extending both radially and chordally in the template area between the optic zone and the body periphery.

6. Apparatus in accordance with claim 2 wherein said fixation means comprises a suction cup secured to the template body, one cup at each end of a body diameter.

* * * * *